United States Patent [19]

Plummer

[11] Patent Number: 5,008,277
[45] Date of Patent: Apr. 16, 1991

[54] N-[(ALPHA-PERHALOALKYLBENZYLOXY)PYRIDYL]-N'-BENZOYLUREA INSECTICIDES

[75] Inventor: Ernest L. Plummer, Yardley, Pa.

[73] Assignee: FMC Corporation, Philadelphia, Pa.

[21] Appl. No.: 374,902

[22] Filed: Jun. 30, 1989

Related U.S. Application Data

[60] Division of Ser. No. 136,045, Dec. 21, 1989, Pat. No. 4,870,089, which is a continuation-in-part of Ser. No. 801,365, Nov. 25, 1985, abandoned.

[51] Int. Cl.$^5$ ............... C07D 213/75; C07D 405/12; A01N 43/40
[52] U.S. Cl. .................................. 514/337; 514/338; 514/346; 546/292; 546/269; 546/270
[58] Field of Search .................. 514/338, 346, 337; 546/270, 292, 269

[56] References Cited

U.S. PATENT DOCUMENTS

| | | | |
|---|---|---|---|
| 4,013,717 | 3/1977 | Wellinga et al. | 564/44 |
| 4,173,639 | 11/1979 | Suhr | 514/349 |
| 4,264,605 | 4/1981 | Suhr et al. | 514/352 |
| 4,350,706 | 9/1982 | Brouwer et al. | 514/594 |
| 4,521,426 | 6/1985 | Cain | 514/346 |
| 4,540,578 | 9/1985 | Chou et al. | 514/349 |

FOREIGN PATENT DOCUMENTS 0113247  7/1984  European Pat. Off. ............ 546/292

Primary Examiner—Alan L. Rotman
Attorney, Agent, or Firm—S. M. Back; M. D. Pintzuk; H. R. Ertelt

[57] ABSTRACT

N-[(Alpha-perhaloalkylbenzyloxy)pyridyl]-N'-benzoylurea compounds of the following structural formula are useful insecticides:

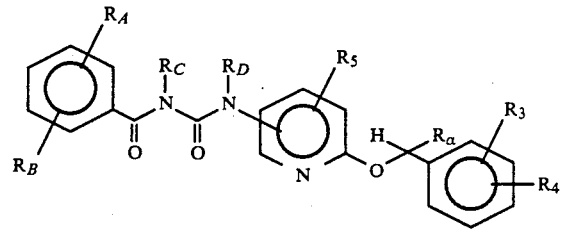

in which
$R_A$ is selected from the group consisting of -hydrogen, -halogen, -lower alkyl, -lower alkoxy, -benzyl, and -benzyloxy;
$R_B$ is selected from -hydrogen and -halogen;
$R_C$ and $R_D$ are both -hydrogen or together constitute a —COCO— bridge;
R is a perhaloalkyl substitutent;
$R_3$ is selected from the group consisting of -hydrogen, -halogen and -phenylthio;
$R_4$ is selected from the group consisting of -hydrogen, -halogen, -lower alkyl, -lower alkoxy, -lower alkoxyalkyl, -lower haloalkoxy, -lower alkylthio, -lower alkylsulfonyl, and -diallylamino; or
$R_3$ and $R_4$ at adjacent ring positions constitute a —OCH$_2$O—, —CH$_2$C(CH$_3$)$_2$O—, or —CF$_2$CF$_2$O— bridge; and
$R_5$ is —hydrogen or -lower alkyl.

23 Claims, No Drawings

N-[(ALPHA-PERHALOALKYLBENZYLOXY)-PYRIDYL]-N'-BENZOYLUREA INSECTICIDES

This application is a division, of application Ser. No. 07/136,045, filed Dec. 21, 1987, now U.S. Pat. No. 4,870,089, which in turn is a continuation-in-part of Ser. No. 06/801,365, filed Nov. 25, 1985, now abandoned.

This invention pertains to the field of benzoylurea insecticides; more specifically, it pertains to novel N-[(alpha-perhaloalkylbenzyloxy)pyridyl]-N'-benzoylurea insecticides, processes and intermediates thereto, insecticidal compositions containing such benzoylurea compounds, and to the use of such compounds for controlling insects.

Certain N-[substituted pyridinyl]-N'-benzoylurea compounds are known as insecticides. For example, U.S. Pat. No. 4,173,639 and U.S. Pat. No. 4,264,605 describe such N'-benzoylurea compounds carrying a N-pyridyl substituent in which the pyridine ring also contains a hydrocarbyloxy group. It is reported that compounds of this type affect insects by interfering with their metamorphosis; that is, they disrupt the normal growth and development pattern.

According to the present invention, adding an alpha-perhaloalkyl substituent to the benzyl group provides insecticides with enhanced activity, controlling certain insects at application rates as low as 1 ppm. Accordingly, the N-[(alpha-perhaloalkylbenzyloxy)pyridyl]-N'-benzoylurea compounds of this invention are described by the formula

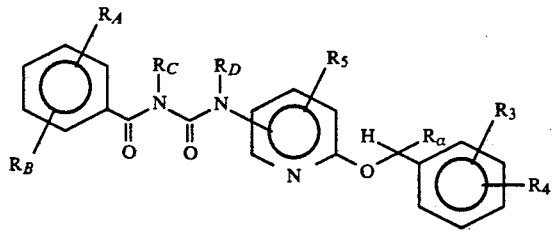

in which $R_A$ is selected from the group consisting of -hydrogen, -halogen, -lower alkyl, -lower alkoxy, -benzyl, and -benzyloxy;

$R_B$ is selected from -hydrogen and -halogen;

$R_C$ and $R_D$ are both -hydrogen or together constitute a -COCO- bridge;

R is a perhaloalkyl substituent;

$R_3$ is selected from the group consisting of -hydrogen, -halogen and -phenylthio;

$R_4$ is selected from the group consisting of -hydrogen, -halogen, -lower alkyl, -lower alkoxy, -lower alkoxyalkyl, -lower haloalkoxy, -lower alkylthio, -lower, alkylsulfonyl, and -dialllylamino; or $R_3$ and $R_4$ at adjacent ring positions constitute a $—OCH_2O—$, $—CH_2C(CH_3)_2O—$, or $—CF_2CF_2O—$ bridge; and $R_5$ is -hydrogen or -lower alkyl.

The terms "halo" and "halogen" when employed herein mean fluorine, chlorine or bromine. The term "lower" modifying "alkyl," "alkoxy," and the like implies a straight or branched hydrocarbon chain of 1–6, preferably 1–3, carbon atoms; "halo" coupled with another term means one or more hydrogen atoms has been replaced by halogen; "perhalo" coupled with another term means all the hydrogen atoms have been replaced by halogen.

Among the aforesaid compounds, the most attractive insecticides results when $R_A$ and $R_B$ are in the 2-and 6-positions, respectively. In addition, N-(3-pyridinyl) compounds are preferred, with $R_5$ at the 5-position. Additionally, the preferred compounds have the $R_3$ and $R_4$ substituents in the 3- and 4-positions, respectively. Specific compounds of interest include N-[[[[2-(2,2,2-trifluoro-1-phenylethoxy)-3-methyl]pyridin-5-yl]amino]carbonyl]-2-chlorobenzamide, N-[[[[2-(2,2,2-trifluoro-1-phenylethoxy)-3-methyl]pyridin-5-yl]amino]carbonyl]-2-fluorobenzmide, N-[[[[2-[1-(2,3-dihydro-2,2,3,3-tetrafluorobenzofuran-5-yl)]-2,2,2-trifluoroethoxy]-pyridin-5-yl]amino]carbonyl]-2,6-difluorobenzamide, N-[[[[2-(2,2,2-trifluoro-1-phenylethoxy)-3-methyl]pyridin-5-yl]amino]carbonyl]-2,6-difluorobenzamide, N-[[[[2-[1-(1,3-benzodiox-5-yl)-2,2,3,3,4,4,4-heptafluorobutoxy]-3-methyl]pyridin-5-yl]amino]carbonyl]2,6-difluorobenzamide, N-[[[[2-[1-(2,3-dihydro-2,2-dimethylbenzofuran-5-yl)-2,2,3,3,3-pentafluoropropoxy]-3-methyl]pyridin-5-yl]amino]carbonyl]-2,6-difluorobenzamide, 1-[(2,6-difluorophenyl)carbonyl]-3-[2-[1-(1,3-benzodiox-5-yl)-2,2,2-trifluoroethoxy]pyridin-5-yl]imidazolidinetrione, 1-[(2,6-difluorophenyl)carbonyl]-3-[[2-(1-phenyl-2,2,2-trifluoroethoxy)-3-methyl]pyridin-5-yl]imidazolidinetrione, N-[[[[2[2,2,2-trifluoro-1-(4-trifluoromethoxyphenyl)ethoxy]3-methyl]pyridin-5-yl]amino]carbonyl]-2,6-difluorobenzamide, and N-[[[[2-[2,2,2-trifluoro-1-(4-trifluoromethoxyphenyl)ethoxy]-3-methyl]pyridin-5-yl]amino]carbonyl]-2-chlorobenzamide.

Also within the contemplation of the instant invention are insecticidal compositions comprising an insecticidally effective amount of at least one of the aforesaid benzoylurea compounds in admixture with an agriculturally acceptable carrier. In addition, this invention includes a method of controlling insects which comprises applying to plants upon which the insects feed and where control is desired an insecticidally effective amount of at least one of the aforesaid N-[(alpha-perhaloalkylbenzyloxy)pyridyl]-N'-benzoylurea compounds.

The compounds of this invention can be prepared using general techniques disclosed in U.S. Pat. No. 4,013,717, viz:

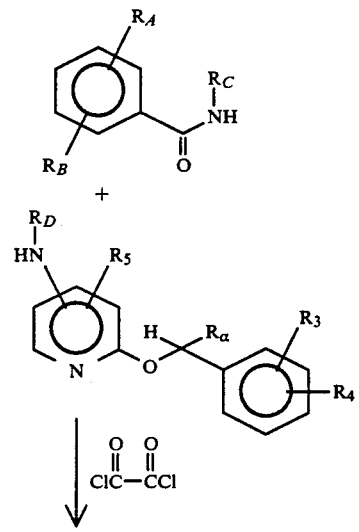

-continued

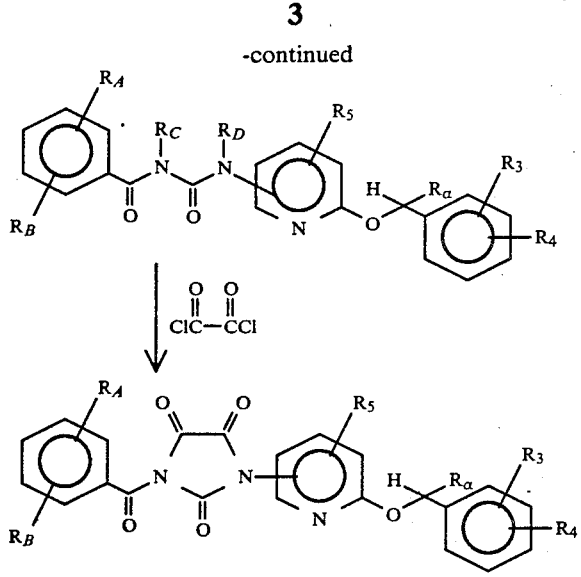

Preparation of the compounds of this invention will be clarified by reference to the following Examples.

EXAMPLE 27

N-[[[2-[1-(2,3-Dihydro-2,2-dimethylbenzofuran-5-yl)-2,2,3,3,3-pentafluoropropoxy]-3-methyl]pyridin-5-yl]amino]carbonyl]-2-chorobenzamide 5-Amino-3-methyl-2-[1-(2,3-dihydro-2,2-dimethylbenzofuran-5-yl)-2,2,3,3,3-pentafluoropropoxy]pyridine was prepared from 2,2,3,3,3-pentafluoro-1-(2,3-dihydro-2,2-dimethylbenzofuran-5-yl)propan-1-one, by the method of Example 42. 2-Chloro-3-methyl-5nitropyridine was used in place of 2-chloro-5-nitropyridine.

In a manner similar to Example 42 the reaction of 2-chlorobenzamide (0.6 g, 0.0037 mole), first with oxalyl chloride (0.5 g, 0.0037 mole) in methylene chloride (10 ml) and toluene (70 ml), followed by reaction with 5-amino-3-methyl-2-[1-(2,3-dihydro-2,2,-dimethylbenzofuran-5-yl)-2,2,3,3,3-pentafluoropropoxy]pyridine (1.5 g, 0.0037 mole), yielded 1.6 g of N-[[[[2-[1-(2,3-dihydro-2,2-dimethylbenzofuran-5-yl)2,2,3,3,3-pentafluoropropoxy]-3-methyl]pyridin-5-yl]amino]carbonyl]-2-chlorobenzamide as a solid (mp 141°–143° C.). The nmr and ir spectra were consistent with the proposed structure.

Analysis: Calc'd for $C_{27}H_{23}ClF_5N_3O_4$: C 55.54; H 3.97; Found: C56.10; H 4.17.

EXAMPLE 42

N-[[[2-[1-(3,4-Dichlorophenyl)-2,2,2-trifluoroethyoxy]-pyridin-5-yl]amino]carbonyl]-2,6-difluorobenzamide Under a dry nitrogen atmosphere a mixture of 3,4-dichloro-alpha,alpha,alpha-trifluoroacetophenone (6.4 g, 0.026 mole) and sodium borohydride (2.0 g, 0.052 mole) in ethanol (100 ml) was stirred at room temperature for approximately 18 hours. The solvent was evaporated under reduced pressure leaving a residue which was dissolved in water. The resultant solution was extracted with two 100 ml portions of methylene chloride. The combined extracts were dried over anhydrous magnesium sulfate and filtered. The filtrate was evaporated under reduced pressure, yielding 6.4 g of 1-(3,4-dichlorophenyl)-2,2,2-trifluoroethanol.

Under a dry argon atmosphere a solution of 2-chloro-5-nitropyridine (1.6 g, 0.010 mole) and 1-(3,4-dichlorophenyl)-2,2,2-trifluoroethanol (2.5 g, 0.010 mole) in dimethyl sulfoxide (50 ml) was stirred for five minutes. Potassium carbonate (1.6 g, 0.011 mole) was added to the mixture in one portion. The resultant mixture was stirred at room temperature for approximately 18 hours. The mixture was transferred to a separatory funnel to which was added 50 g of ice and 75 ml of a 2N aqueous sodium hydroxide solution. This aqueous mixture was extracted with two 200 ml portions of diethyl ether. The combined extracts were dried over anhydrous magnesium sulfate and filtered. The solvent was evaporated from the filtrate under reduced pressure, leaving an oil. Purification of this oil by column chromatography on silica gel yielded 3.3 g of 2-[1-(3,4-dichlorophenyl)-2,2,2-trifluoroethoxy]-5-nitropyridine.

Hydrogenation of 2-[1-(3,4-dichlorophenyl)-2,2,2-trifluoroethoxy]-5-nitropyridine (2.7 g, 0.0074 mole) with plantinum oxide (0.3 g, 0.0013 mole) in methanol (50 ml) yielded 2.5 g of 5-amino-2-[1-(3,4-dichlorophenyl)-2,2,2-trifluoroethoxy]pyridine.

A stirred mixture of 2,6-difluorobenzamide (0.56 g, 0.0036 mole), oxalyl chloride (0.45 g, 0.0036 mole), and methylene chloride (10 ml) in toluene (70 ml) was heated at reflux for three hours. Approximately 10 ml of solvent was removed by distillation under reduced pressure. A solution of 5-amino-2-[1-( 3,4-dichlorophenyl)-2,2,2-trifluoroethoxy]pyridine (1.2 g, 0.0036 mole) in toluene (35 ml) was added to the reaction mixture. The resultant solution was stirred at room temperarture for approximately 18 hours. Most of the solvent was evaporated under reduced pressure, leaving a liquid residue. About 150 ml of n-heptane was added to the residue, and the mixture was stirred at room temperature, slowly forming a precipitate. The mixture was cooled in dry ice before collecting the precipitate by filtration. A total of 1.65 g of N-[[[2-[-1-(3,4-dichlorophenyl)2,2,2-trifluoroethoxy]pyridin-5-yl]amino]carbonyl]2,6-difluorobenzamide was collected (mp 171°–172° C.). The nmr and ir spectra were consistent with the proposed structure.

Analysis: Calc'd for $C_{21}H_{12}Cl_2F_5N_3O_3$: C 48.48; H 2.33; Found: C 48.62; H 2.60.

EXAMPLE 66

N-[[[2-[1-(2,2,3,3-Tetrafluorobenzofuran-5-yl)-2,2,2-trifluoroethoxy]-3-methyl]pyridin-5-yl]amino]carbonyl]-2,6-difluorobenzamide 5-Amino-3-methyl-2-(2,2,3,3-tetrafluorobenzofuran-5-yl)-2,2,2-trifluoroethoxy]pyridine was prepared from 1-(2,2,3,3-tetrafluorobenzofuran-5-yl)2,2,2-trifluoroethanone by the method of Example 42. The latter starting material was obtained as follows:

Into a pressure bottle was placed 2-chloro-4nitrophenol (15.0 g, 0.086 mole), potassium carbonate (11.9 g, 0.86 mole), propanethiol (1.5 g, 0.02 mole), 1,2-dibromotetrafluoroethane (33.7 g, 0.13 mole), and N,N-dimethylformamide (115 ml). The pressure bottle was sealed, and the mixture was stirred at 50° C. for 48 hours. The pressure bottle was cooled to room temperature, opened, and the contents poured into a separatory funnel. Approximately 200 ml of a 2N aqueous sodium hydroxide solution was added to the separatory funnel. The resultant mixture was extracted with four 300 ml portions of diethyl ether. The extracts were combined and washed with two 100 ml portions of a 2N aqueous sodium hydroxide solution. The washed extract was dried over anhydrous magnesium sulfate and filtered. The filtrate was evaporated under reduced pressure, leaving an oil. The reaction described above was repeated three additional times. The residual oils form the four experiments were combined and purified by column chromatography on silica gel, eluting with n-heptane:toluene (95:5), yielding 57.6 g of 3-chloro-4-bromo-1,1,2,2-tetrafluoroethoxy)nitrobenzene as an oil.

Into a pressure bottle were placed 3-chloro-4-(2-bromo-1,1,2,2-tetrafluoroethoxy)nitrobenzene (10.0 g, 0.028 mole), copper powder (9.0 g, 0.14 mole, 200 mesh), 2,2'-bipyridyl (0.45 g, 0.0028 mole), and dimethylsulfoxide (40 ml). The pressure bottle was sealed and the reaction mixture was stirred at 190°195° C. for two hours. The pressure bottle was cooled to room temperature, opened, and the contents poured, into a separatory funnel. Approximately 200 ml o a 2N hydrochloric acid solution was added to the separatory funnel. The mixture was extracted with three 150 ml portions of diethyl ether. The extracts were combined and washed in succession with 200 ml of a 2N hydrochloric acid solution, 200 ml of a saturated aqueous sodium chloride solution, and 200 ml of a 2N aqueous sodium hydroxide solution. The washed extract was dried over anhydrous magnesium sulfate and filtered. The solvent was evaporated under reduced pressure, leaving an oil. The reaction described above was repeated six additional times. The residual oils from the seven experiments were combined and subjected to column chromatography on silica gel, eluting with toluene, yielding a yellow oil. This oil was dissolved in 125 ml methylcyclohexane, and the solution was placed in a freezer for approximately 18 hours. Crystals formed and were collected by filtration, yielding 20.7 g of 2,2,3,3-tetrafluoro-5-nitorbenzofuran. The filtrate was evaporated under reduced pressure, leaving an oil. Distillation of this oil under reduced pressure provided an additional 3.0 g of product (bp 75° C./0.2 mm Hg).

Hydrogenation of 2,2,3,3-tetrafluoro-5-nitrobenzene (10.0 g, 0.042 mole) with a catalytic amount of platinum oxide (0.5 g) in methanol (200 ml) produced 8.6 g of 5-amino-2,2,3,3-tetrafluorobenzofuran.

A stirred mixture of 5-amino-2,2,3,3-tetrafluorobenzofuran (5.0 g, 0.024 mole) and hydrobromic acid (7.3 ml of a 48% aqueous solution) and water (10 ml) was cooled to 3° C. in an ice bath. While maintaining a temperature of less than 5° C., a solution of sodium nitrite (1.7 g, 0.024 mole) in water was added. After complete addition this mixture was stirred for a brief period, then was added slowly to a stirred, refluxing mixture of cuprous bromide (6.9 g, 0.024 mole) in hydrobromic acid (10 ml of a 48% aqueous solution). After complete addition the mixture was stirred at reflux for 20 minutes, then allowed to cool to room temperature. The reaction mixture was poured into a separatory funnel and diluted with ice water. This mixture was extracted several times with diethyl ether. The extracts were combined and washed first with 100 ml of an aqueous saturated sodium chloride solution, then with two 100 ml portions of a 2N aqueous sodium hydroxide solution. The washed organic phase was dried over anhydrous magnesium sulfate and filtered. The filtrate was evaporated at atmospheric pressure, yielding 5.9 g of 5-bromo-2,2,3,3-tetrafluorobenzofuran as an oil.

The reaction of 5-bromo-2,2,3,3-tetrafluorobenzofuran (5.3 g, 0.02 mole) with magnesium turnings (0.48 g) in dry diethyl ether was followed by reaction with N-methoxy-N-methyltrifluoroacetamide (3.5 g, 0.022 mole), yielding 5.3 g of 1-(2,2,3,3-tetrafluorobenzofuran-5-yl)-2,2,2-trifluoroethanone.

In a manner similar to Example 42 the reaction of 2,6-difluorobenzamide (0.3 g, 0.0019 mole), first with oxalyl chloride (0.3 g, 0.0021 mole) in methylene chloride (5 ml) and toluene (50 ml), followed by reaction with 5-amino-3-methyl-2-[1-(2,2,3,3-tetrafluorobenzofuran-5-yl)-2,2,2-trifluoroethoxy]pyridine (0.8 g, 0.0019 mole) yielded 0.8 g of N-[[[2-[1-(2,2,3,3-tetrafluorobenzofuran-5-yl)-2,2,2-trifluoroethoxy]-3-methyl]pyridine-5-yl]amino]carbonyl]2,6-difluorobenzamide as an oil. The nmr and ir spectra were consistent with the proposed structure.

Analysis: Calc'd for $C_{24}H_{14}F_9N_3O_4$: C 49.75; H 2.43; Found: C 47.47; H 2.26.

EXAMPLE 84

1-[(2,6-Difluorophenyl)carbonyl]-3-[2-[1-(3,4-dichlorophenyl)-2,2,2-trifluoroethoxy]pyridine-5-yl]imidazolidinetrione To a stirred solution of N-[[[2-[1-(3,4-dichlorophenyl)-2,2,2-trifluoroethoxy]pyridin-5-yl]amino]carbonyl]2,6-difluorobenzamide (1.0 g, 0.002 mole) in 1,2-dichloroethane (10 ml) was added oxalyl chloride (0.24 g, 0.0020 mole). This mixture was heated at reflux for five days. Additional oxalyl chloride (0.24 g) was added, and refluxing was continued for one more day. The solvent was removed from the reaction mixture by distillation under reduced pressure, leaving an oil. This oil was purified by column chromatography on silica gel, elution with toluene: ethyl acetate (9:1), yielding 0.84 g of 1-[(2,6-difluorophenyl)carbonyl]-3-[2-[1-(3,4-dichlorphenyl)2,2,2-trifluoroethoxy]pyridin-5-yl]imidazolidinetrione as a solid (mp 160° C.). The nmr and ir spectra were consistent with the proposed structure.

Analysis: Calc'd for $C_{23}H_{10}Cl_2F_3N_3O_5$: C 48.11; H 1.76; Found: C 47.15; H 1.69.

Additional Examples prepared by similar techniques appear in Table 1.

In the normal use of the insecticidal benzoylureas of the present invention, the benzoylureas usually will not be employed free from admixture or dilution, but ordinarily will be used in a suitable formulated composition compatible with the method of application and comprising an insecticidally effective amount of benzoylurea. The benzoylureas of this invention, like most pesticidal agents, may be blended with the agriculturally acceptable surface-active agents and carriers normally employed for facilitating the dispersion of active ingredients, recognizing the accepted fact that the formulation and mode of application of an insecticide may affect the activity of the material. The present benzoylureas may be applied, for example, as sprays, dusts, or granules to the area where pest control is desired, the type of application varying of course with the pest and the environment. Thus, the benzoylureas of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for the benzoylureas. The granule particles are relatively large, a diameter of about 400-2500 microns typically. The particles are either impregnated with the benzoylurea from solution or coated with the benzoylurea, adhesive sometimes being employed. Granules generally contain 0.05–10%, preferably 0.5–5%, active ingredient as the insecticidally effective amount.

Dusts are admixtures of the benzoylureas with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the insecticide. These finely divided solids have an average particle size of less than about 50 microns. A typical dust formulation useful for controlling insects contains 1 part of benzoylurea, such as N-[[[[2-(2,2,2-trifluoro-1-phenylethoxy)-3-methyl]pyridin-5-yl]amino]carbonyl]-2-chlorobenzamide, and 99 parts of talc.

The benzoylureas of the present invention may be made into liquid concentrates by dissolution or emulsification in suitable liquids and into solid concentrates by admixture with talc, clays, and other known solid carriers used in the pesticide art. The concentrates are compositions containing, as an insecticidally effective amount, about 5–50% benzoylurea, such as N-[[[[2-(2,2,2-trifluoro-1-phenylethoxy)-3-methyl]pyridin-5-yl]amino]carbonyl]-2-chlorobenzamide, and 95–50% inert material, which includes surfaceactive dispersing, emulsifying, and wetting agents, but even higher concentrations of active ingredient may be employed experimentally. The concentrates are diluted with water or other liquids for practical application as sprays, or with additional solid carrier for use as dusts.

Typical carriers for solid concentrates (also called wettable powders) include fuller's earth, clays, silicas, and other highly absorbent, readily wetted inorganic diluents. A solid concentrate formulation useful for controlling insects contains 1.5 parts each of sodium lignosulfonate and sodium laurylsulfate as wetting agents, 25 parts of N-[[[[2-(2,2,2-trifluoro-1-phenylethoxy)-3-methyl]pyridin-5-yl]amino]carbonyl]-2-chlorobenzamide, and 72 parts of attapulgite clay.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the benzoylurea with a liquid or solid emulsifying agent, or they may also contain a liquid carrier such as xylene, heavy aromatic naphthas, isophorone and other relatively non-volatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium slats; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce.

The surface-active agent, when used, normally comprises about 1–15% by weight of the insecticidal composition.

Other useful formulations include simple solutions of the active ingredient in a solvent in which it is completely soluble at the desired concentration, such as acetone or other organic solvents.

An insecticidally effective amount of benzoylurea in an insecticidal composition diluted for application is normally in the range of about 0.001% to about 8% by weight. Many variations of spraying and dusting compositions known in the art may be used by substituting the benzoylureas of this invention into compositions known or apparent in the art.

The insecticidal compositions of this invention may be formulated with other active ingredients, including other insecticides, nematicides, acaricides, fungicides, plant growth regulators, fertilizers, etc. In using the compositions to control insects, it is only necessary that an insecticidally effective amount of benzoylurea be applied to plants upon which insects feed and whose control is desired. For most applications, an insecticidally effective amount will be about 0.1–2.0 kg/ha.

The benzoylureas of this invention were tested by incorporating the compounds into the diet of second instar southern armyworm (*Spodoptera eridania*) and cabbage looper (*Trichoplusia ni*). The tests were conducted at rates of 200, 20, and 2 ppm, using ten larvae per replicate and two replicates per rate. Each test was read one day, three to five days, and six to eleven days after infestation to determine the number dead after at least one molt.

The test media consisted of a clay formulation (dust) of the test compound mixed with the insect diet. The components of the test media were:

|  | Parts by Weight |
| --- | --- |
| Pinto beans | 12.90 |
| Wheat germ | 5.68 |
| Brewer's dried yeast | 3.64 |
| Ascorbic acid | 0.37 |
| Methyl paraben | 0.23 |
| Sorbic acid | 0.11 |
| Sodium benzoate | 0.00284 |
| Agar | 0.71 |
| Formalin (40%) | 0.23 |
| Water | 76.13 |
|  | 100.00 |

The agar was dissolved with heating in one-half the water and was brought to a boil. Simultaneously, all other ingredients except the formalin were placed in a blender with the remaining water and were reduced to a smooth, homogenous mixture. This mixture was added to the boiling agar. Immediately, the formalin was added with mixing.

The compounds of this invention were formulated as a dust on a clay base. The dust consisted of the following:

| Clay Formulation | 5% Dust |
| --- | --- |
| Test compound | 5.00 |
| Base | 95.00 |
| 96% Attaclay | |
| 2% highly purified sodium lignosulfonate (100%) | |
| 2% powdered sodium alkyl- | |

| Clay Formulation | 5% Dust |
|---|---|
| naphthalene sulfonate (75%) | 100.00 |

These formulations were prepared by mixing the active ingredient (i.e. the test compound) with the dry base.

Test media containing 200 ppm of the test compound were prepared by making a 'stock solution' from 1000 mg of a 5% dust formulation stirred well with 5 ml of distilled water in a vial. One milliliter of the 'stock solution' was added to 50 ml of warm, i.e. molten, insect diet in a plastic petri dish which was then mixed thoroughly. After cooling to room temperature, the gelled test media were infested with test larvae and covered.

Lower test rates were prepared by dilution of the 'stock solution' according to the following table:

| Desired Rate (ppm) | ml of 'stock solution' | ml of water |
|---|---|---|
| 20 | 1 | 9 |
| 2 | 1 ml of 20 ppm solution | 9 |

The results of diet incorporated testing are summarized in Table 2.

TABLE 1

Insecticidal N-[(Alpha-perhaloalkylbenzyloxy)pyridyl]-N'-benzoylureas

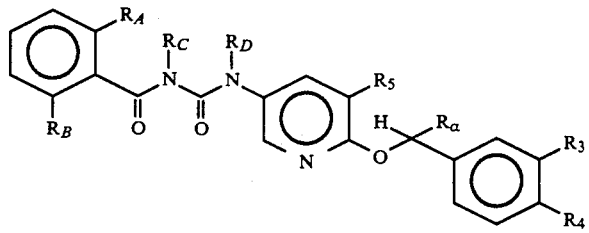

| Example | $R_A$ | $R_B$ | $R_5$ | R | $R_3$ | $R_4$ | mp (°C.) |
|---|---|---|---|---|---|---|---|
| 1 | H | H | $CH_3$ | $CF_3$ | H | H | 155–158 |
| 2 | H | Cl | H | $CF_3$ | H | H | 162–163 |
| 3 | H | Cl | H | $C_2F_5$ | H | H | 149–149.5 |
| 4 | H | Cl | H | $C_3F_7$ | H | H | 129 |
| 6 | H | Cl | H | $CF_3$ | $SC_6H_5$ | H | 161–163 |
| 7 | H | Cl | H | $C_3F_7$ | H | $SCH_3$ | 124–127 |
| 8 | H | Cl | H | $CF_3$ | Cl | Cl | 111–112 |
| 9 | H | Cl | H | $C_2F_5$ | Cl | Cl | 129–131 |
| 10 | H | Cl | H | $C_3F_7$ | Cl | Cl | 119–123 |
| 11 | H | Cl | H | $CF_3$ | —OCH$_2$O— | | 116–119 |
| 12 | H | Cl | H | $C_2F_5$ | —OCH$_2$O— | | 121 |
| 13 | H | Cl | H | $C_3F_7$ | —OCH$_2$O— | | 145 |
| 14 | H | Cl | H | $C_2F_5$ | —CH$_2$C(CH$_3$)$_2$O— | | 149–154 |
| 15 | H | Cl | H | $C_3F_7$ | —CH$_2$C(CH$_3$)$_2$O— | | 163–163.5 |
| 16 | H | Cl | $CH_3$ | $CF_3$ | H | H | 142–145 |
| 17 | H | Cl | $CH_3$ | $C_2F_5$ | H | H | 124–125 |
| 18 | H | Cl | $CH_3$ | $C_3F_7$ | H | H | |
| 20 | H | Cl | $CH_3$ | $CF_3$ | H | Cl | 115 |
| 21 | H | Cl | $CH_3$ | $CF_3$ | Cl | Cl | |
| 22 | H | Cl | $CH_3$ | $C_2F_5$ | Cl | Cl | 90–94 |
| 23 | H | Cl | $CH_3$ | $C_3F_7$ | Cl | Cl | 131–133 |
| 24 | H | Cl | $CH_3$ | $CF_3$ | —OCH$_2$O— | | |
| 25 | H | Cl | $CH_3$ | $C_2F_5$ | —OCH$_2$O— | | 144 |
| 26 | H | Cl | $CH_3$ | $C_3F_7$ | —OCH$_2$O— | | 63 |
| 27 | H | Cl | $CH_3$ | $C_2F_5$ | —CH$_2$C(CH$_3$)$_2$O— | | 141–143 |
| 28 | H | Cl | $CH_3$ | $C_3F_7$ | —CH$_2$C(CH$_3$)$_2$O— | | 152–155 |
| 29 | H | Cl | $CH_3$ | $C_3F_7$ | Cl | N(CH$_2$CH=CH$_2$)$_2$ | oil |
| 30 | H | F | $CH_3$ | $CF_3$ | H | H | |
| 31 | H | $CH_3$ | $CH_3$ | $CF_3$ | H | H | 122–123 |
| 32 | H | $C_2H_5$ | $CH_3$ | $CF_3$ | H | H | 103–104 |
| 33 | H | $CH_2C_6H_5$ | $CH_3$ | $CF_3$ | H | H | 89–91 |
| 34 | H | $OCH_3$ | $CH_3$ | $CF_3$ | H | H | 139–142 |
| 35 | H | $OCH_2C_6H_5$ | $CH_3$ | $CF_3$ | H | H | 104–106 |
| 36 | F | F | H | $CF_3$ | H | H | 172–174 |
| 37 | F | F | H | $C_2F_5$ | H | H | 193–195 |
| 38 | F | F | H | $C_3F_7$ | H | H | 137 |
| 40 | F | F | H | $CF_3$ | $SC_6H_5$ | H | 102–103.5 |
| 41 | F | F | H | $C_3F_7$ | H | $SCH_3$ | 132–135 |
| 42 | F | F | H | $CF_3$ | Cl | Cl | 171–172 |
| 43 | F | F | H | $C_2F_5$ | Cl | Cl | 164–167 |
| 44 | F | F | H | $C_3F_7$ | Cl | Cl | 158–160 |
| 45 | F | F | H | $CF_3$ | —OCH$_2$O— | | 165–167 |
| 46 | F | F | H | $C_2F_5$ | —OCH$_2$O— | | 183 |
| 47 | F | F | H | $C_3F_7$ | —OCH$_2$O— | | 103 |
| 48 | F | F | H | $CF_3$ | —CH$_2$C(CH$_3$)$_2$O— | | 122 |
| 49 | F | F | H | $C_2F_5$ | —CH$_2$C(CH$_3$)$_2$O— | | 163–167 |
| 50 | F | F | H | $C_3F_7$ | —CH$_2$C(CH$_3$)$_2$O— | | 164–167 |
| 51 | F | F | H | $CF_3$ | —CF$_2$CF$_2$O— | | 162–163.5 |
| 52 | F | F | $CH_3$ | $CF_3$ | H | H | 143–145 |

TABLE 1-continued

Insecticidal N-[(Alpha-perhaloalkylbenzyloxy)pyridyl]-N'-benzoylureas

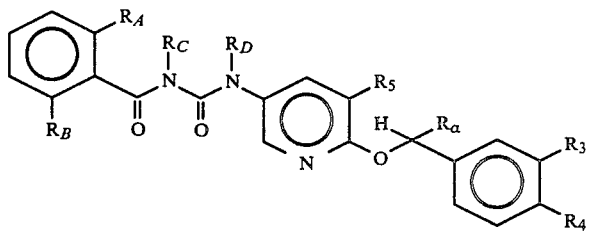

| Example | $R_A$ | $R_B$ | $R_5$ | R | $R_3$ | $R_4$ | mp (°C.) |
|---|---|---|---|---|---|---|---|
| 53 | F | F | $CH_3$ | $C_2F_5$ | H | H | 121–122 |
| 54 | F | F | $CH_3$ | $C_3F_7$ | H | H | 102 |
| 56 | F | F | $CH_3$ | $CF_3$ | H | Cl | 145 |
| 57 | F | F | $CH_3$ | $CF_3$ | Cl | Cl | |
| 58 | F | F | $CH_3$ | $C_2F_5$ | Cl | Cl | 119–122 |
| 59 | F | F | $CH_3$ | $C_3F_7$ | Cl | Cl | 132–132.5 |
| 60 | F | F | $CH_3$ | $CF_3$ | | $-OCH_2O-$ | 167 |
| 61 | F | F | $CH_3$ | $C_2F_5$ | | $-OCH_2O-$ | 144 |
| 62 | F | F | $CH_3$ | $C_3F_7$ | | $-OCH_2O-$ | 94 |
| 63 | F | F | $CH_3$ | $CF_3$ | | $-CH_2C(CH_3)_2O-$ | 115 |
| 64 | F | F | $CH_3$ | $C_2F_5$ | | $-CH_2C(CH_3)_2O-$ | 135–140 |
| 65 | F | F | $CH_3$ | $C_3F_7$ | | $-CH_2C(CH_3)_2O-$ | 140–143 |
| 66 | F | F | $CH_3$ | $CF_3$ | | $-CF_2CF_2O-$ | oil |
| 67 | Cl | F | $CH_3$ | $CF_3$ | H | H | 171–175 |
| 68 | Cl | $CH_3$ | $CH_3$ | $CF_3$ | H | H | 164–167 |
| 69 | F | F | H | $CClF_2$ | H | H | 191–192 |
| 70 | F | F | $CH_3$ | $CClF_2$ | H | H | 107–110 |
| 71 | F | F | $CH_3$ | $C_3F_7$ | Cl | $N(CH_2CH=CH_2)_2$ | oil |
| 72 | F | F | $CH_3$ | $CClF_2$ | F | $CH_3$ | 163–165 |
| 73 | H | 3-F | $CH_3$ | $CF_3$ | H | H | 180–181 |
| 74 | H | 7-F | $CH_3$ | $CF_3$ | H | H | |
| 77* | H | Cl | H | $CF_3$ | H | $SC_6H_5$ | |
| 78* | H | Cl | H | $C_3F_7$ | H | $SCH_3$ | |
| 79* | H | Cl | H | $CF_3$ | Cl | Cl | 149–152 |
| 80* | H | Cl | H | $CF_3$ | | $-OCH_2O-$ | 134 |
| 81* | H | Cl | $CH_3$ | $CF_3$ | H | H | |
| 82* | H | Cl | $CH_3$ | $C_2F_5$ | H | H | |
| 83* | F | F | H | $C_3F_7$ | H | $SCH_3$ | |
| 84* | F | F | H | $CF_3$ | Cl | Cl | 160 |
| 85* | F | F | H | $CF_3$ | | $-OCH_2O-$ | 164 |
| 86* | F | F | H | $C_2F_5$ | | $-CH_2C(CH_3)_2O-$ | 184 |
| 87* | F | F | $CH_3$ | $CF_3$ | H | H | 67 |
| 88* | F | F | $CH_3$ | $C_2F_5$ | H | H | |
| 89 | Cl | H | $CH_3$ | $CF_3$ | H | $OC_2H_5$ | 167 |
| 90 | F | F | $CH_3$ | $CF_3$ | H | $OC_2H_5$ | 137 |
| 91 | Cl | H | $CH_3$ | $CF_3$ | H | $CH_2OCH_3$ | 163–167 |
| 92 | Cl | H | $CH_3$ | $CF_3$ | H | $SCH_3$ | 151 |
| 93 | F | F | $CH_3$ | $CF_3$ | H | $SCH_3$ | 151 |
| 94 | Cl | H | $CH_3$ | $CF_3$ | H | $SO_2CH_3$ | 134 |
| 95 | F | F | $CH_3$ | $CF_3$ | H | $SO_2CH_3$ | 180 |
| 96 | F | F | $CH_3$ | $CF_3$ | H | $OCF_3$ | 161 |
| 97 | Cl | H | $CH_3$ | $CF_3$ | H | $OCF_3$ | 139 |
| 98 | F | F | $CH_3$ | $CF_3$ | H | $CH_2OCH_3$ | 140–144 |

*$R_C$ and $R_D$ together constitute a $-COCO-$ bridge.

TABLE 2

Diet Incorporated Tests
% Kill
(5% Formulation on Clay)

| Cpd. of Ex. | Exposure Period (Days) | Insects Tested[a] and Rate | | | | | |
|---|---|---|---|---|---|---|---|
| | | SAW (ppm) | | | CL (ppm) | | |
| | | 200 | 20 | 2 | 200 | 20 | 2 |
| 1 | 5 | 100 | 100 | 0 | 100 | 100 | 10 |
| 2 | 4 | 70 | 80 | 60 | 100 | 100 | 90 |
| 3 | 5 | 100 | 100 | 100 | 100 | 100 | 80 |
| 4 | 4 | 90 | 90 | 90 | 100 | 100 | 80 |
| 6 | 4 | 100 | 0 | 10 | 20 | 0 | 0 |
| 7 | 4 | 100 | 70 | 0 | 60 | 10 | 0 |
| 8 | 4 | 0 | 50 | 70 | 100 | 100 | 0 |
| 9 | 3 | 60 | 100 | 30 | 100 | 70 | 0 |
| 10 | 4 | 90 | 100 | 70 | 100 | 0 | 0 |
| 11 | 8 | 20 | 0 | 0 | 100 | 100 | 0 |
| 12 | 6 | 60 | 10 | 0 | 100 | 60 | 20 |
| 13 | 5 | 90 | 30 | 0 | 90 | 40 | 0 |
| 14 | 6 | 10 | 100 | 0 | 90 | 10 | 0 |
| 15 | 7 | 100 | 100 | 90 | 100 | 40 | 0 |
| 16 | 5 | 90 | 100 | 100 | 100 | 100 | 100 |
| 17 | 5 | 100 | 100 | 100 | 100 | 100 | 100 |
| 18 | 4 | 70 | 100 | 0 | 100 | 100 | 0 |
| 20 | 4 | 100 | 100 | 100 | 100 | 100 | 90 |
| 21 | 4 | 10 | 60 | 0 | 80 | 0 | 0 |
| 22 | 7 | 100 | 100 | 60 | 100 | 90 | 10 |
| 23 | 4 | 100 | 80 | 60 | 80 | 0 | 0 |
| 24 | 4 | 60 | 50 | 0 | 10 | 80 | 10 |

TABLE 2-continued

Diet Incorporated Tests
% Kill
(5% Formulation on Clay)

| Cpd. of Ex. | Exposure Period (Days) | SAW (ppm) 200 | SAW (ppm) 20 | SAW (ppm) 2 | CL (ppm) 200 | CL (ppm) 20 | CL (ppm) 2 |
|---|---|---|---|---|---|---|---|
| 25 | 3 | 0 | 50 | 0 | 90 | 40 | 0 |
| 26 | 6 | 80 | 60 | 0 | 100 | 40 | 10 |
| 27 | 8 | 100 | 60 | 0 | 100 | 70 | 0 |
| 28 | 4 | 100 | 80 | 30 | 50 | 0 | 0 |
| 29 | 8 | 10 | 30 | 10 | 10 | 0 | 0 |
| 30 | 4 | 100 | 80 | 20 | 90 | 100 | 30 |
| 31 | 5 | 100 | 100 | 100 | 100 | 100 | 20 |
| 32 | 8 | 50 | 10 | 0 | 0 | 0 | 0 |
| 33 | 8 | 0 | 0 | 0 | 0 | 0 | 10 |
| 34 | 5 | 100 | 0 | 0 | 0 | 0 | 10 |
| 35 | 8 | 30 | 0 | 0 | 10 | 0 | 0 |
| 36 | 4 | 70 | 80 | 60 | 100 | 100 | 90 |
| 37 | 5 | 100 | 90 | 100 | 100 | 100 | 100 |
| 38 | 7 | 90 | 100 | 100 | 90 | 100 | 100 |
| 40 | 5 | 30 | 50 | 10 | 90 | 80 | 0 |
| 41 | 5 | 100 | 100 | 0 | 100 | 100 | 10 |
| 42 | 4 | 60 | 60 | 90 | 80 | 100 | 80 |
| 43 | 3 | 80 | 90 | 60 | 100 | 80 | 30 |
| 44 | 4 | 100 | 100 | 100 | 100 | 100 | 0 |
| 45 | 5 | 10 | 10 | 20 | 90 | 80 | 10 |
| 46 | 6 | 100 | 100 | 0 | 100 | 100 | 0 |
| 47 | 5 | 30 | 50 | 10 | 90 | 80 | 0 |
| 48 | 4 | 100 | 100 | 80 | 90 | 80 | 80 |
| 49 | 8 | 100 | 100 | | 50 | 60 | 10 |
| 50 | 4 | 90 | 100 | 60 | 100 | 100 | 0 |
| 51 | 5 | 100 | 100 | 100 | 100 | 100 | 100 |
| 52 | 5 | 100 | 100 | 100 | 100 | 100 | 100 |
| 53 | 5 | 90 | 100 | 100 | 100 | 100 | 100 |
| 54 | 4 | 70 | 90 | 100 | 100 | 100 | 100 |
| 56 | 4 | 100 | 100 | 100 | 80 | 90 | 70 |
| 57 | 4 | 40 | 70 | 90 | 20 | 40 | 0 |
| 58 | 7 | 100 | 100 | 90 | 100 | 100 | 10 |
| 59 | 4 | 100 | 100 | 90 | 100 | 100 | 10 |
| 60 | 4 | 30 | 30 | 0 | 90 | 30 | 0 |
| 61 | 3 | 10 | 50 | 10 | 100 | 80 | 0 |
| 62 | 6 | 70 | 50 | 0 | 100 | 90 | 0 |
| 63 | 4 | 100 | 100 | 70 | 80 | 100 | 80 |
| 64 | 2 | 20 | 0 | 0 | 40 | 40 | 0 |
| 65 | 4 | 100 | 100 | 50 | 100 | 30 | 0 |
| 66 | 4 | 60 | 70 | 100 | 100 | 100 | 90 |
| 67 | 4 | 100 | 100 | 100 | 90 | 100 | 40 |
| 68 | 5 | 100 | 100 | 0 | 100 | 100 | 10 |
| 69 | 4 | 100 | 100 | 80 | 100 | 100 | 100 |
| 70 | 4 | 90 | 100 | 90 | 100 | 100 | 80 |
| 71 | 8 | 70 | 20 | 30 | 0 | 0 | 10 |
| 72 | 5 | 100 | 100 | 60 | 100 | 80 | 70 |
| 73 | 4 | 0 | 10 | 0 | 0 | 0 | 0 |
| 74 | 4 | 70 | 0 | 0 | 20 | 10 | 10 |
| 77 | 4 | 80 | 0 | 0 | 100 | 0 | 0 |
| 78 | 4 | 100 | 0 | 0 | 100 | 0 | 0 |
| 79 | 9 | 100 | 100 | 40 | 100 | 100 | 20 |
| 80 | 8 | 0 | 70 | 20 | 100 | 30 | 0 |
| 81 | 5 | 100 | 100 | 0 | 100 | 90 | 0 |
| 82 | 5 | 90 | 100 | 10 | 100 | 100 | 0 |
| 83 | 4 | 100 | 100 | 0 | 100 | 80 | 0 |
| 84 | 4 | 100 | 90 | 40 | 100 | 80 | 0 |
| 85 | 8 | 90 | 10 | | 100 | 40 | 10 |
| 86 | 8 | 60 | 0 | 10 | 50 | 0 | 0 |
| 87 | 3 | 70 | 80 | 100 | 100 | 90 | 80 |
| 88 | 5 | 100 | 100 | 10 | 90 | 90 | 70 |
| 89 | 5 | | | | 100 | 85[b] | 75[c] |
| 90 | 5 | | | | 100 | 100[b] | 100[c] |
| 91 | 5 | | | | 100 | 90[b] | 45[c] |
| 92 | 5 | | | | 100 | 0 | 0 |
| 93 | 5 | | | | 100 | 15 | 0 |
| 94 | 5 | | | | 95 | 10 | 0 |
| 95 | 5 | | | | 95 | 25 | 0 |
| 96 | 5 | | | | 100 | 100 | 75 |
| 97 | 5 | | | | 100 | 100 | 100 |
| 98 | 5 | | | | 100 | 95[b] | 50[c] |

[a]SAW = Southern armyworm
CL = Cabbage looper
[b]10 ppm
[c]5 ppm

What is claimed is:

1. An insecticidal benzoylurea compound of the formula

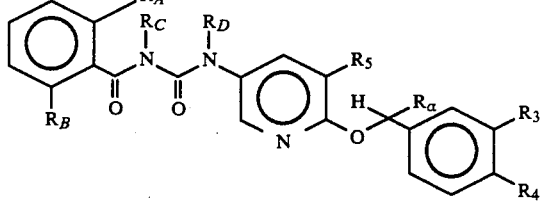

wherein
R$_A$ is selected from the group consisting of -hydrogen, -halogen, -lower alkyl, -lower alkoxy, -benzyl, and -benzyloxy;
R$_B$ is selected from -hydrogen and -halogen;
R$_C$ and R$_D$ together constitute a —COCO— bridge;
Rα is a lower perhaloalkyl substituent;
R$_3$ is selected from the group consisting of -hydrogen, -halogen and -phenylthio, and R$_4$ is selected from the group consisting of -hydrogen, -halogen, -lower alkyl, -lower alkoxy, -lower alkoxyalkyl, -lower haloalkoxy, -lower alkylthio, -lower alkylsulfonyl, and -diallylamino; or R$_3$ and R$_4$ together constitute a —OCH$_2$O—, —CH$_2$C(CH$_3$)$_2$O—, or —CF$_2$CF$_2$O— bridge; and
R$_5$ is —hydrogen or —lower alkyl.

2. An insecticidal compound of claim 1 wherein
R$_3$ is selected from the group consisting of -hydrogen, —halogen and —phenylthio; and
R$_4$ is selected from the group consisting of -hydrogen, -halogen, -lower alkyl, -lower alkoxy, -lower alkoxyalkyl, -lower haloalkoxy, -lower alkylthio, -lower alkylsulfonyl, and -diallylamino.

3. An insecticidal compound of claim 1 wherein R$_3$ and R$_4$ together constitute a —OCH$_2$O—, —CH$_2$C(CH$_3$)$_2$O—, or —CF$_2$CF$_2$O— bridge.

4. 1-[(2,6-difluorophenyl)carbonyl]-3-[2-[1-(1,3-benzodiox-5-yl)-2,2,2-trifluoroethoxy]pyridin-5-yl]imidazolidinetrione, a compound of claim 1.

5. 1-[(2,6-difluorophenyl)carbonyl]-3-[[2-(1-phenyl2,2,2-trifluoroethoxy)-3-methyl]pyridin-5-yl]imidazolidinetrione, a compound of claim 1.

6. An insecticidal composition comprising in admixture with an agriculturally acceptable carrier a compound of the formula

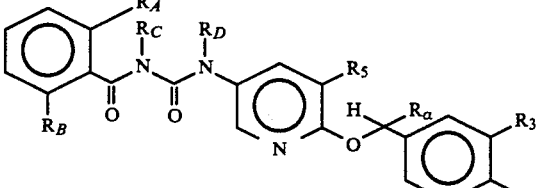

wherein
R$_A$ is selected from the group consisting of -hydrogen -halogen, -lower alkyl, -lower alkoxy, -benzyl, and -benzyloxy;
R$_B$ is selected from -hydrogen and -halogen;
R$_C$ and R$_D$ together constitute a —COCO— bridge;
Rα is a lower perhaloalkyl substituent;

$R_3$ is selected from the group consisting of -hydrogen, -halogen and -phenylthio, and $R_4$ is selected from the group consisting of -hydrogen, -halogen, -lower alkyl, -lower alkoxy, -lower alkoxyalkyl, -lower haloalkoxy, -lower alkylthio, -lower alkylsulfonyl, and -diallylamino; or $R_3$ and $R_4$ together constitute a —OCH$_2$O—, —CH$_2$C(CH$_3$)$_2$O—, or —CF$_2$CF$_2$O— bridge; and $R_5$ is -hydrogen or -lower alkyl.

7. An insecticidal composition of claim 6 wherein $R_3$ is selected from the group consisting of -hydrogen, -halogen and -phenylthio; and $R_4$ is selected from the group consisting of -hydrogen, -halogen, -lower alkyl, -lower alkoxy, -lower alkoxyalkyl, -lower haloalkoxy, -lower alkylthio, -lower alkylsulfonyl, and -diallylamino.

8. An insecticidal composition of claim 6 wherein $R_3$ and $R_4$ together constitute a —OCH$_2$O—, —CH$_2$C(CH$_3$)$_2$O—, or —CF$_2$CF$_2$O— bridge.

9. An insecticidal composition of claim 6 wherein said compound is 1-[(2,6-difluorophenyl)carbonyl[-3-[2-[1-(1,3-benzodiox-5-yl)-2,2,2-trifluoroethoxy]pyridin-5-yl]imidazolidinetrione.

10. A method for controlling insects which comprises applying to plants upon which insects feed and whose control is desired an insecticidally effective amount of a compound of the formula

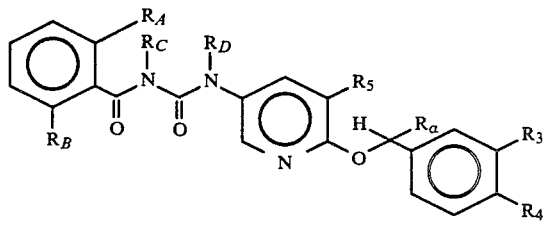

wherein
$R_A$ is selected from the group consisting of -hydrogen, -halogen, -lower alkyl, -lower alkoxy, -benzyl, and -benzyloxy;
$R_B$ is selected from -hydrogen and -halogen;
$R_C$ and $R_D$ together constitute a -COCO- bridge;
$R_a$ is a lower perhaloalkyl substituent;
$R_3$ is selected from the group consisting of -hydrogen, -halogen and -phenylthio, and $R_4$ is selected from the group consisting of -hydrogen, -halogen, -lower alkyl, -lower alkoxy, -lower alkoxyalkyl, -lower haloalkoxy, -lower alkylthio, -lower alkylsulfonyl, and -diallylamino; or $R_3$ and $R_4$ together constitute a —OCH$_2$O—, —CH$_2$C(CH$_3$)$_2$O—, or —CF$_2$CF$_2$O— bridge; and $R_5$ is -hydrogen or -lower alkyl.

11. The method of claim 10 wherein
$R_3$ is selected from the group consisting of -hydrogen, -halogen and -phenylthio; and
$R_4$ is selected from the group consisting of -hydrogen, -halogen, -lower alkyl, -lower alkoxy, -lower alkoxyalkyl, -lower haloalkoxy, -lower alkylthio, -lower alkylsulfonyl, and -diallylamino.

12. The method of claim 10 wherein $R_3$ and $R_4$ together constitute a —OCH$_2$O—, —CH$_2$C(CH$_3$)$_2$O—, or —CF$_2$CF$_2$O— bridge.

13. An insecticidal benzoylurea compound of the formula

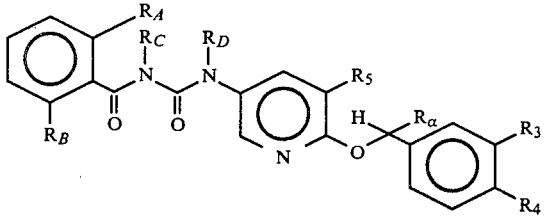

wherein
$R_A$ is selected from the group consisting of -hydrogen, -halogen, -lower alkyl, -lower alkoxy, -benzyl, and -benzyloxy;
$R_B$ is selected from -hydrogen and -halogen;
$R_C$ and $R_D$ are both -hydrogen;
$R_a$ is a lower perhaloalkyl substituent;
$R_3$ and $R_4$ together constitute a —OCH$_2$O—, —CH$_2$C(CH$_3$)$_2$O—, or —CF$_2$CF$_2$O— bridge; and
$R_5$ is -hydrogen or -lower alkyl.

14. N-[[[[2-[1-(2,3dihydro-2,2,3,-tetrafluorobenzofuran-5-yl)]-2,2,2-trifluoroethoxy]pyridin-5-yl]amino]carbonyl]-2,6-difluorobenzamide, a compound of claim 13.

15. N-[[[[2-[1-(1,3-benzodiox-5-yl)-2,2,3,3,4,4,4-heptafluorobutoxy]-3-methyl]pyridin-5-yl]amino]carbonyl]-2,6-difluorobenzamide, a compound of claim 13.

16. An insecticidal composition comprising in admixture with an agriculturally acceptable carrier a compound of the formula

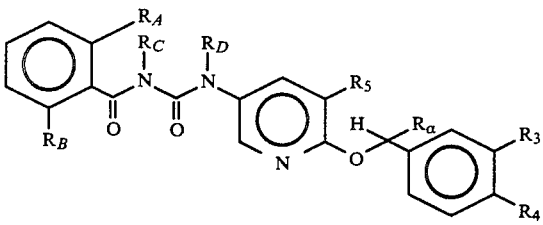

wherein
$R_A$ is selected from the group consisting of -hydrogen, -halogen, -lower alkyl, -lower alkoxy, -benzyl, and -benzyloxy;
$R_B$ is selected from -hydrogen and -halogen;
$R_C$ and $R_D$ are both -hydrogen;
$R_a$ is a lower perhaloalkyl substituent;
$R_3$ and $R_4$ together constitute a —OCH$_2$O—, —CH$_2$C(CH$_3$)$_2$O—, or —CF$_2$CF$_2$O— bridge; and
$R_5$ is -hydrogen or -lower alkyl.

17. An insecticidal composition of claim 16 wherein said compound is N-[[[[2-[1-(2,3-dihydro-2,2,3,3-tetrafluorobenzolfuran-5-yl)]-2,2,2-trifluoroethoxy 2,6-difluorobenzamide.

18. An insecticidal composition of claim 17 wherein said compound is N-[[[[2-[1-(1,3-benzodiox-5-yl-2,2,3,3,4,4,4-heptafluorobutoxy]-3-methyl]pyridin-5-yl]amino]carbonyl]-2,6-difluorobenazmide.

19. An insecticidal composition of claim 17 wherein said compound is N-[[[[2-[1-(2,3-dihydro-2,2-dimethylbenzofuran-5yl)- 2,2,3,3,3-pentafluoropropoxy]-3-methyl]pyridin-5-yl]amino]carbonyl]-2,6-difluorobenzamide.

20. A method for controlling insects which comprises applying to plants upon which insects feed and whose control is desired an insecticidally effective amount of a compound of the formula

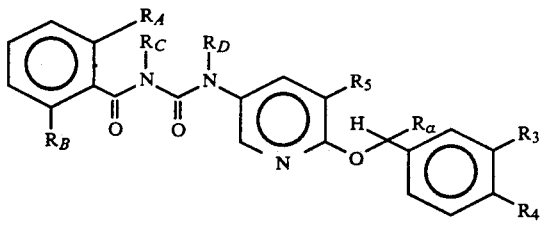

wherein $R_A$ is selected from the group consisting of -hydrogen, -halogen, -lower alkyl, -lower alkoxy, -benzyl, and -benzyloxy;

$R_B$ is selected from -hydrogen and -halogen;

$R_C$ and $R_D$ are both -hydrogen;

$R\alpha$ is a lower perhaloalkyl substitutent;

$R_3$ and $R_4$ together constitute a —OCH$_2$O—, —CH$_2$C(CH$_3$)$_2$O—, or —CF$_2$CF$_2$O— bridge; and $R_5$ is -hydrogen or -lower alkyl.

21. The method of claim 20 wherein said compound is N-[[[2-[1-(2,3-dihydro-2,2,3,3-tetrafluorobenzofuran-5-yl)]-2,2,2-trifluoroethoxy]pyridin-5-yl]amino]arbonyl]-2,6difluorobenzamide.

22. The method of claim 20 wherein said compound is N-[[[2-[1-(1,3-benzodiox-5yl)-2,2,3,3,4,4,4-heptafluorobutoxy]-3-methyl]pyridin-5yl]amino]carbonyl]-2,6-difluorobenzamide.

23. The method of claim 20 wherein said compound is N-[[[2-[1-(2,3-dihydro-2,2-dimethylbenzofuran-5-yl)-2,2,3,3,3-pentafluoropropoxy]-3-methyl]pyridin-5-yl]amino]carbonyl]-2,6-difluorobenzamide.

* * * * *